Figure 1:
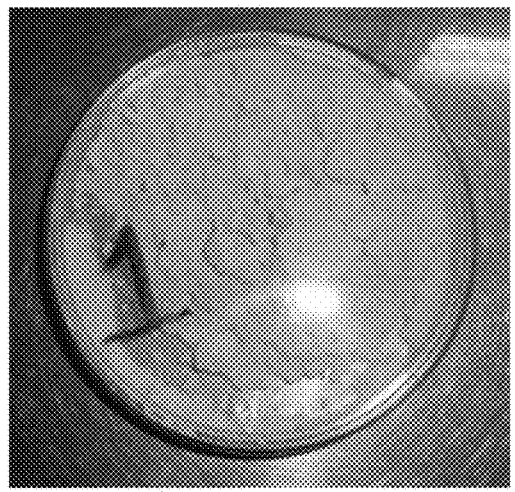
Figure 1:
Figure 1:
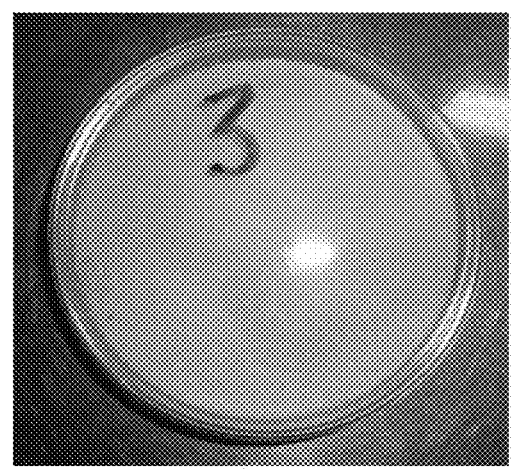
Figure 2:
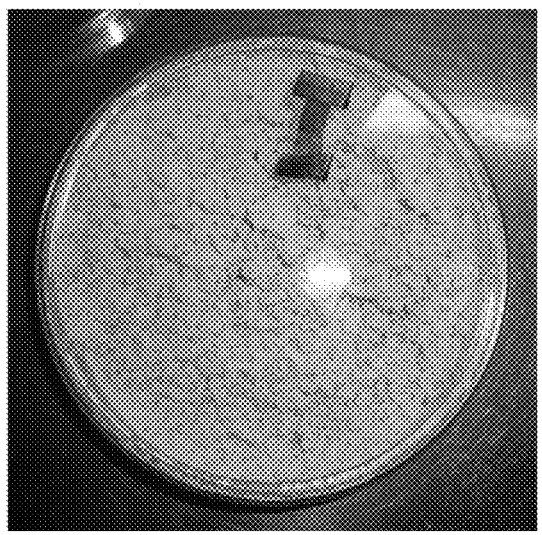
Figure 2:
Figure 2:

US010413613B2

(12) United States Patent
Choza Romero

(10) Patent No.: US 10,413,613 B2
(45) Date of Patent: Sep. 17, 2019

(54) NEBULISATION-BASED METHOD FOR MIXING SUBSTANCES

(71) Applicant: Andrés Abelino Choza Romero, Zapopan (MX)

(72) Inventor: Andrés Abelino Choza Romero, Zapopan (MX)

(*) Notice: Subject to any disclaimer, the term of this patent is extended or adjusted under 35 U.S.C. 154(b) by 217 days.

(21) Appl. No.: 15/309,653

(22) PCT Filed: May 25, 2015

(86) PCT No.: PCT/MX2015/000078
§ 371 (c)(1),
(2) Date: Nov. 8, 2016

(87) PCT Pub. No.: WO2016/006991
PCT Pub. Date: Jan. 14, 2016

(65) Prior Publication Data

US 2017/0266298 A1 Sep. 21, 2017

(30) Foreign Application Priority Data

Jul. 7, 2014 (MX) .................... MX/a/2014/008314

(51) Int. Cl.

| | |
|---|---|
| *A61K 47/42* | (2017.01) |
| *A61K 9/19* | (2006.01) |
| *A23L 15/00* | (2016.01) |
| *A61K 8/64* | (2006.01) |
| *A61K 31/192* | (2006.01) |
| *A61K 31/196* | (2006.01) |
| *A61K 31/407* | (2006.01) |
| *A61K 31/525* | (2006.01) |
| *A61K 31/616* | (2006.01) |
| *A61Q 17/04* | (2006.01) |
| *A23B 5/02* | (2006.01) |
| *A61K 9/12* | (2006.01) |
| *A61K 9/16* | (2006.01) |
| *A61K 8/98* | (2006.01) |

(52) U.S. Cl.
CPC ................ *A61K 47/42* (2013.01); *A23B 5/02* (2013.01); *A23L 15/00* (2016.08); *A23L 15/30* (2016.08); *A61K 8/64* (2013.01); *A61K 8/981* (2013.01); *A61K 9/12* (2013.01); *A61K 9/1658* (2013.01); *A61K 9/1664* (2013.01); *A61K 31/192* (2013.01); *A61K 31/196* (2013.01); *A61K 31/407* (2013.01); *A61K 31/525* (2013.01); *A61K 31/616* (2013.01); *A61Q 17/04* (2013.01); *A23V 2002/00* (2013.01)

(58) Field of Classification Search
CPC ...... A61K 8/64; A61K 31/192; A61K 31/196; A61K 31/407; A61K 31/525; A61K 31/616; A61K 9/1658; A61K 9/1664; A61K 8/981; A61K 51/00; A61K 9/16; A61K 9/50; A61K 9/00; A61K 2300/00; A61K 9/0073; A61K 9/12; A61K 47/6921; A61K 47/6941; A61K 8/046; A61K 47/42; A23L 15/30; A23L 15/00; A61B 5/055
See application file for complete search history.

(56) References Cited

U.S. PATENT DOCUMENTS

| | | | | |
|---|---|---|---|---|
| 3,393,074 A * | 7/1968 | Ehrlich | A21D 2/364 | 426/523 |
| 6,630,121 B1 * | 10/2003 | Sievers | A61K 9/1694 | 424/1.13 |
| 2005/0196513 A1 * | 9/2005 | Lewis | A23L 15/20 | 426/614 |

* cited by examiner

*Primary Examiner* — Hong T Yoo
(74) *Attorney, Agent, or Firm* — Shutts & Bowen LLP

(57) ABSTRACT

The invention relates to a method for producing a mixture containing a hydrated egg product and a substance of interest, wherein the mixing is carried out by means of ultrasonic nebulization. The method comprises: beating at least one egg product until it is in a foam state; adding at least one substance of interest, in the form of a pressurized mist, to the foamy egg product; mixing until an emulsified mixture in a foam state is obtained; suctioning the emulsified mixture in order to transfer same to a dehydrator; dehydrating the emulsified mixture until a moisture level no greater than 5% is obtained; grinding the emulsified mixture to the desired grain size distribution; and sterilizing the ground mixture. The invention also relates to the mixtures produced using said method, and to the products containing said mixture.

22 Claims, 3 Drawing Sheets

M1

M2

M3

M1

M2

M3

M1

M2

M3

NEBULISATION-BASED METHOD FOR MIXING SUBSTANCES

TECHNICAL FIELD OF THE INVENTION

The present invention is related with the technical fields of chemistry, food, pharmaceutics and cosmetics, preferably, since it provides a procedure to obtain mixes of substances through pressurized or ultrasonic nebulization, as well as the mixes obtained with said procedure and the products contained in said mixes.

BACKGROUND OF THE INVENTION

Several techniques for the preparation of products in the form of micro granules have been developed. In them, the mix of active substances and excipients can be subjected to a procedure of mixing, kneading, spheronization, coating, etc. So, there is equipment for palletization, coating dishes, fluid bed machines, extrusion machines, centrifuges, and others.

In the patent documents EP247983 y EP244380, the active substance is kneaded by wet process with a mixture of excipients that allows to create and alkaline microenvironment. The mixture is then extruded and spheronized. The spheronized microgranules are coated with one or more intermediated layers of water soluble, alkaline, buffering, polymeric excipients, later an outer gastro-resistant layer is applied.

Patent ES2052697 shows an example of coating with dust distributed with the use of roto-granules. Spherical granules are described, that have a nucleus clad with dust that contains a benzimidazolium anti-ulceric compound and hidroxypropyl cellulose of low grade of substitution. A procedure to produce the aforementioned spherical granules is also described, that is characterized because the nuclei are wetted by nebulization with an agglutinant solution and sprinkled with a dust containing the active substance. The pharmaceutical preparations and food supplements, prepared with these techniques, present the difficulty of liberation of the active substance.

In the publication WO1999006032 a pharmaceutical preparation is described, that comprehends an inert nucleus, an active layer that is water soluble or of rapid disintegration in water that was obtained from an aqueous or hydroalcoholic solution. A procedure is also described, which is carried out through the coating of the inert nuclei through the nebulization of the aqueous or hydroalcoholic suspension, the drying of the active layer formed during the nebulization of the previous step, the coating of the charged nuclei through an external gastro-resistant layer.

In the publication U.S. Pat. No. 5,585,050 micro capsules that contain at least one active substance are described, which is constituted by an internal, hydrophilic, essentially non-aqueous nucleus, formed from the dissolution of, at least, one active substance that is water soluble and amphoteric in, at least, one non-aqueous hydrophilic solvent, and from a wall that encompasses the internal nucleus based on, at least, one polymer or copolymer. These micro capsules have application in systems of instantaneous release of the active ingredient, such as hygiene items, gloves and surgery materials.

The document ES2080703 describes stabilization methods of drug substances incorporated to gum tablets, which consist of micro-encapsulation of the active drug substance or substances, through a product of micro-encapsulation, whose main component is egg albumin and in which glycyrrhizinate ammonium, aspartame, iso-octane, deionized water and span. The active substances are dissolved separately, along with albumin, glycyrrhizinate ammonium and aspartame in deionized water, with the later addition of iso-octane and span, and stirring to form an emulsion that is heated up to 60° C. and is applied to a sieve of square apertures; leaving it in conditions to be incorporated, by conventional methods, to the gum mass.

The document ES2209973 refers to a combination that comprehends glucosamine and hyper-immunized egg, where the combination can be concomitant or a mixture. The methods for its mixing are conventional, not alluding the use of an ultrasonic nebulizing equipment for the mixing.

According to the results of the study of the art, several companies and research centers dedicated to the production of isolated proteins from egg fractions, are interested in creasing and diversify the use of some components, such as ovalbumin and ovotransferin. Particularly, the industries dedicated to the production of lysozyme, used as an antimicrobial agent, that obtain as byproducts other nitrogenated low cost fractions, generally destined for animal feeding or for their use as emulsifier and gelifier in diverse foods.

On the other hand, many properties have been discovered on flavonoids (flavones, flavonols, flavonones, flavonol, antoganins and isoflavones), such as, antioxidants, antiallergenic, anti-inflammatory, antibiotic and anti-viral. Scientific studies have indicated that those actions are performed through the mechanism of action modulation of enzymatic activity, inhibition of malignant-cell proliferation, inhibition of the enzyme lipoxygenase that transforms arachidonic acid on leukotrienes, which mediate allergenic and inflammatory processes, as well as inhibition of the enzyme ATPase, dependent on calcium and the AMP phosphodiesterase, which act in conjunction for the liberation of histamine, with which the allergenic reaction takes place.

The flavonoid's potential protector has been shown over two main mechanisms, which with oxidative stress and inflammation, through the inhibition of interleukin, tumor necrosis factor alpha and inducible oxide synthase.

Recent studies indicate that the ingestion of flavonoids improves cognitive processes, particularly learning and memory, associated to the activation of molecular signaling cascades that promote synaptic plasticity and neurogenesis in regions of cognitive interest, like hippocampus and brain cortex.

BRIEF DESCRIPTION OF FIGURES

FIG. 1 is a comparative of normal the coloring, between three methods of mixing, of a chicken egg albumin mixture with riboflavin.

FIG. 2 is a comparative of the coloring between three methods of mixing, from a mixture of chicken egg albumin with riboflavin, previously subjected to ozone conditions.

FIG. 3 is a comparative of coloring under UV light, between three methods of mixing, from a mixture of chicken egg albumin with riboflavin.

DETAILED DESCRIPTION OF THE INVENTION

The details characteristic of the present invention are clearly shown in the following description, figures and examples included, which are merely illustrative of one of the preferred modalities of the performance of the inventions; thus, they must not be considered as a limitation for it.

The present invention provides a procedure to mix substances through the technique of nebulization. An example of those substances are fractions of bird's eggs with another substance, preferably an active compound, for example a drug, food, food supplement, cosmetic, to mention some of them all. Where the egg fraction functions as a transporter vehicle of the active compound. For which, formulations or mixtures, obtained by said method, and the products that contain said mixtures are provided.

Under this context, we will obtain pharmaceutical, food, cosmetics, formulations which depends on the compound considered as active that is mixed with some egg product; by this way a better absorption or advantageous use of the active substance is achieved.

As fraction or egg product, the principal components of a fowl's egg are included, such as yolk, egg white, shell and the possible combinations between them, as well as the egg white-, yolk- and shell-derived fractions, which are separated, isolated or purified by conventional techniques, of the principal components of the egg, for example, proteins, hormones, vitamins, lipids, carbohydrates, salts, minerals, etc.

The preferred fowl's eggs are those of chicken, although eggs from other birds can also be used like quail, turkey, duck, pheasant, goose, guinea-fowl, ostrich, and others.

In the pharmaceutical formulations, we have those related to ophthalmology, to state some, ophthalmologic solutions that are lubricants, anti-inflammatory, analgesic and antibiotics, preferably.

The starting point is the research carried away in reference to the fact that the egg white is closely related to the elements contained in a human teardrop, since it also contains lysozymes, lactalbumin, collagen, minerals, vitamins and mainly a similar pH value.

The egg white or albumin has a pH value of 8, it represents an approximate 60% of the total weight of the egg; and around 12% of the egg white are solids, of which, an 85% are proteins, that after separating them, can have numerous applications. Among these proteins, the following can be used: ovalbumin, which is a phosphoglycoprotein, which represents around 60% of the total protein of the egg white, the ovotransferrin, with two electrophoretic forms in a ratio of 4:1, it represents 12% of the protein, the ovomucoid which is a glycoprotein that represents 11% of the protein, the lysozyme which has three electrophoretic forms and represents 3.4% of the protein, the ovomucin which is a fibrous glycoprotein and gelling agent and has three electrophoretic forms, the ovoglobulins are two forms that represent 8% and the ovoinhibitor that represents 1.5% of the protein.

Specifically, the present invention refers to a procedure for the preparation of pharmaceutical products, food products, food supplements and cosmetic products, preferably, through the absorption of, at least, a substance of interest in, at least, an egg product through an efficient mixing and incorporation process, with the technology of nebulization, be it pressurized and/or ultrasonic, etc.

The procedure of the present invention is advantageous because the obtained products are easily absorbed by the receptor tissue, for example, the intestinal tract, skin, ocular tissue, etc. with no adverse effects and good overall tolerance. The procedure reduces the price of their obtention when compared to other chemical or enzymatic methods.

The procedure of the invention comprehends the following steps:

This procedure can be carried away using, at least, a recently obtained product (hydrated) from an egg or dehydrated from a common, commercialized product, like commercial albumin. In case of using commercial egg products, their quality must be verified, in order to obtain the expected results.

When the egg product is dehydrated, first it must be hydrated with a hydrating liquid, such as water, lipidic mixture, aqueous or hydro-alcoholic extract, depending of the type of the egg product, in a ratio of six parts of the hydrating liquid per one part of the dehydrated egg product during approximately 5 minutes, with a slow stirring of 50 rpm, in average.

When recently obtained egg White and/or the yolk are used, no hydration is required.

Once the product has been completely hydrated, then it gets shaken, first with a stirring of 1000 rpm until turning it into a foamy state, which usually happens after one or two minutes.

On another step, the active compound or of interest to be mixed with the egg product, is placed on the deposit of a nebulizing equipment, be it pressurized or a conventional ultrasonic, to be added to the egg product in the form of pressurized fog; to do this, the speed of the stirring is increased to 3000-4000 rpm for three or four minutes until an emulsified mixture in form of foam is achieved.

The substances of interest may be as solid particles finely sieved or dissolved in aqueous and/or hydro-alcoholic extracts.

Said active substance of interest can be any substance that provides a benefit for an animal, including the human, and that is compatible to be transported by an egg product. For example it can be a chemical substance, like a medicinal active compound that prevents, controls, treats or cures some physiological, physical or other alterations.

Among the pharmaceutically acceptable active compounds are the urinary acidifiers, analgesics, androgens; anesthetics; anorexigens; antacids; anti-acne; Antiadrenals; antianginal; antiarrhythmic; anti-arthritis; Anti-arthrosic; antiasthmatic; antibacterials; anticoagulants; Anti-cholelithiasic; contraceptives; anticonvulsants; antidiarrheal; Anti-dyskinetic; antidiuretic; antidotes; antiemetics; antispasmodics; anti-spasticity; antifibrotic; anti-flatulent; antifungals; anti-glaucomic; anti-gouty; anti-influenza; anthelmintics; Antihaemorrhagics; antihemorrhoidal; Antihyperkalemic; antihypercholesterolemic; antihyperlipemic; Anti-hyperoxaluric; Anti-hyperpotassemic; Antihyperprolactemic; antihypertensives; Antihyperthyroidic; Antihhyperuricemic; Antihypocalcemic; Anthypocholesterloemic; antihypotensive; antihistamines; Anti-inflammatory; antiheadache; antileprosy; antilithic; antimalarials; antimyasthenics; antifungals; antineoplastic; antirheumatic; Antiscabies; antiseborrhoeic; antiseptics; antithyroid; antituberculosis; antitussives; antiulcer; Antiurolithiasic; antivaricose; antivertiginosos; antivirals;

Neuromuscular blockers; bronchodilators; capilaryprotectant; cardiotonic; cycloplegic; cytotoxic; cholelitholytics; decongestants; diuretics; emetics; escabicides; steroid; Gastric Motility stimulants; C.N.S. Stimulants; germicides; hypocholesterolaemiant; hypoglycemic; lipid-lowering; hormones; Dopaminergic inhibitors; Gonadotrophe inhibitors; Childbirth inhibitors; Inhibitors of gastric secretions; immunosuppressants; laxatives; mydriatic; Miotic Myelosuppressives-; mucolytics; orexigens; oxytocics; pediculicide; placebos; prophylactics; and any and all possible combinations between them.

Among the analgesics it can be the acetylsalicylic acid, among the anti-inflammatories it can be the diclofenac, sodium naproxen, ketorolac and any combination.

It can also be a food supplement, such as vitamins, antioxidants, hormones, sweeteners, like stevia, and others.

It is here where a fine mix (nano-mix) of the interest compound with the egg product is achieved, where the integration is more efficient, than through mixing without ultrasonic nebulizing equipment.

The emulsified mixture in form of foam is drawn in with a pumping system into an adequate dehydrating container that complies with the regulations to dehydrate foods components, dehydrating it for 50 min, at 68 to 70° C., followed by grinding to obtain the desired granulometry.

The obtained final product is subjected to ultraviolet radiation, with a UV lamp for 30 minutes in a closed box, preferably.

Optionally, the obtained product can be bottled, compressed to form a tablet, encapsulated, deposited into a sachet, etc.

Of the total weight of the hydrated mixture (egg product plus active compound of interest) approximately a 14% of said mixture is obtained but already dehydrated.

When the egg white is used, it is hydrated with a lipidic mixture.

It is worth pointing out that all the procedure is carried away under innocuous conditions, according to good manufacturing practices In the case of albumin, the stability of the formed foam is due to the ovomucin, which forms a film of insoluble material. Formation of foam is presented when denaturing of the protein molecules occurs in a way in which polypeptide chains have their longitudinal axis parallel to the surface. That change of molecular configuration results in the loss of solubility of a part of the albumin, which is congregated in the liquid-air interphase. Other properties of egg whites are its anti-crystallizing and agglutinant capabilities In the process of formation of foam from a protein dispersion, the protein must be rapidly absorbed in the interphase to excerpt tensioactive activity. Thus, it is essential that it is soluble and flexible, that has a compound of low molecular weight and that it has and appropriate lipo/hydrophilic balance The stability of the egg foam is determined by the properties of the film, the distribution of the bubble size, temperature, movement to which it is subjected and the nature of the dispersed gaseous phase. The first three factors have a direct relationship with the nature of the solutes that are contained in the aqueous phase (proteins, sugars, polysaccharides and salts).

The presence of particles in the foam provokes an increase of the size of the bubbles, but it leads to a decrease of the foam volume. The big bubbles grow at the expense of the small ones from gas diffusion through the lamella due to the differential pressure between them.

When the active compound of interest is nebulized and added to the albumin in form of foam, it is rapidly dissolved and incorporated into the whole of the foam. In this scenario, the effect of the intermolecular forces of attraction of Van Der Waals appears, that act in short distance and tend to attract the actives present in the nebulized gas.

The equipment or instruments to carry away the method previously described, can be of the equipment or instruments already familiar by an expert in the subject. As it can be seen, a mixing machine, a container to grind the egg product, a nebulizer and a pressurized or ultrasonic nebulizer, a drying system, a vacuum machine with a pumping system, a dehydrator and a UV light chamber are needed. Obviously, the sequence of use of this equipment is established according to the requirements of the procedure; even some adjustments in said machines can be performed in order to improve the procedure and make it faster and more efficient.

The effect of UV light on some bacteria, fungi, virus and other unicellular organisms is widely known, particularly UV light of 260 nanometers, but in the present invention UV light use is proposed only for certain products that are not sensitive to its effects.

Finally, according to the procedure of the invention, the dry product, maximum humidity of 5%, is transferred to a pulverization and capsuling process, or alternatively it can be compressed to form a tablet.

This way we obtain a mixture that contains, at least, an egg product; and at least, an active compound of interest, where said ingredients were mixed by nebulization, through the aforementioned procedure. Thus, this mixture is comprehended in the scope of the present invention.

The obtained mixture can be used as raw material for the generation of pharmaceutical products, food products, food supplements, cosmetics, etc. Where the applications can be very varied, for example: ingestible solutions, ophthalmic solutions, nasal or dermatological solutions, food products, food supplements, nutraceutical products, energizing beverages, etc.

EXAMPLES

Example 1. Process for the Obtention of a Mixture of Stevia *Estevia rebaudiana* Bertoni and Chicken Egg's Dehydrated Albumin The process begins with the hydration of albumin in a steel container, in a ratio of 6 parts of water per each of dehydrated albumin, for 5 minutes with slow stirring of 50 rpm.

Once the albumin is completely hydrated, the procedure continues with the shaking of albumin, first with stirring of 1000 rpm for 1 to 2 minutes; then the filtered aqueous extract of stevia is added to the container of a nebulizing agent by pressure, and the addition of the aqueous extract of stevia through nebulized fog to the hydrated albumin begins, and the stirring increases to 3000-4000 rpm, for 3 to 4 minutes until an emulsified mixture in form of foam is obtained.

The emulsified mixture in form of foam, is then vacuumed with a pump system into a fitting dehydrating container that complies with the regulations to dehydrate food products, dehydrating it for 50 min at 69° C., later it goes through a mill to get ground in order to obtain the desired granulometry.

From the start of the procedure, innocuity conditions were maintained, according to good manufacturing practices in conventional ways, and the final product was subjected to ultraviolet radiation, with a UV mercury lamp at 265 nanometers for 30 minutes in a closed box.

For every 100 g of the hydrated mixture (albumin plus stevia) 14 grams of the dehydrated mixture were obtained. Said mixture can be used as a natural sweetener enriched with the amino acids provided by the albumin, and with a glycemic index of zero.

Example 2. Mixture Tests Between the Method of the Present Inventions, and the Conventional Mixing Methods, Using Three Mixtures of Albumin and Riboflavin Materials and Methods A first mixture of 100 grams of chicken egg albumin and 50 grams of riboflavin was mixed dry-mixed using a method of grinding (M1), through a pulverizing grinder in a conventional 200 mesh. Where the albumin and riboflavin were added to the grinder to be ground at the same time.

A second mixture containing 100 mL of liquid albumin and 50 mL of liquid riboflavin was homogenized through a mixing process using an ultrasonic arm (M2). Where the ultrasonic arm was submerged in the solution to perform the mixing.

The third mixture also contained 100 mL of liquid albumin and 50 mL of liquid riboflavin, and was homogenized by agitation and pressured nebulization, as proposed by the method of the present invention (M3).

Once the three samples were mixed, they were subjected to oxidizing testing using an ozonator, brand ADELO™ which oxygen source is an oxygen generator, brand PULMO AID™ at a flow of 1 L/min and an ozone dosage of 200 mg/h, the results found are explained below.

Results.

The homogenized mixture by grinding showed hyperpigmentation at 15 minutes from initiation of the mixing procedure (M1). This indicated that the mixture was rapidly oxidized, which is inconvenient for said mixture (see figures).

The mixture done with the ultrasonic arm (M2) showed color change from yellow to Brown at the same 15 minutes of exposition to ozone with a very irregular fractioning of riboflavin's fluorescence to exposure of UV. An increase of temperature was detected, which is not convenient since it degraded the albumin. It was also observed that there was not a good combination or mixing of the active compounds (see figures).

Figure 3:
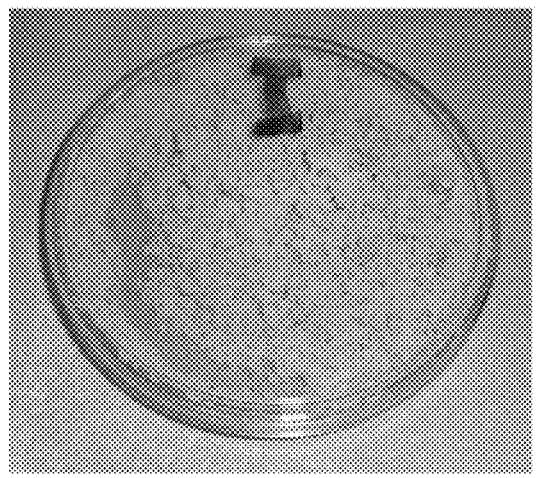
Figure 3:
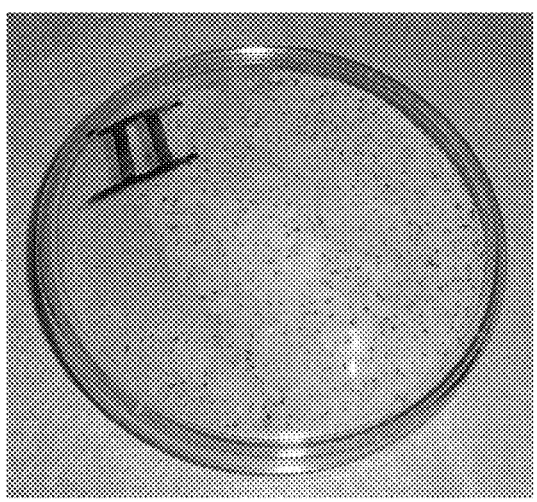
Figure 3:
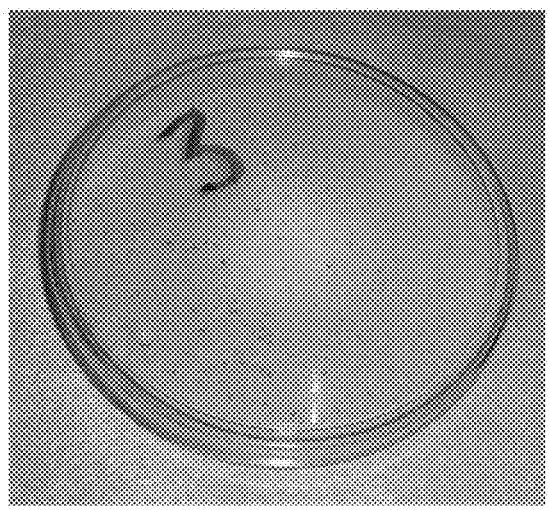

On the other hand, the mixture carried away with the proposed method of the present invention (M3) showed changes only after 37 minutes of exposure to ozone and at exposure to UV it showed a homogeneously distributed luminescence throughout all the surface of the mixture (see FIG. 3). Which indicated us that the oxidation was delayed and there was a good combination between egg albumin and riboflavin, thus there is a guarantee that it can be digested in the site of interest.

CONCLUSION

This leads us to conclude that our process is an ultra-homogenization of active compounds of interest with a transporting vehicle, like the fractions or products of bird's eggs, so that it looks like that is only one product.

The invention claimed is:

1. A method for creating a ground mixture, comprising:
stirring an egg product at 1000 rpm, for 1 to 2 minutes, to convert the egg product to a foamy state;
nebulizing a substance of interest;
mixing, at 3000 to 4000 rpm, the egg product in the foamy state with the nebulized substance of interest, for three to four minutes to yield an emulsified mixture;
dehydrating the emulsified mixture, at a temperature that is 68 to 70° C., for 50 minutes, wherein the dehydrated emulsified mixture has a humidity that is 5% or less;

grinding the dehydrated emulsified mixture to yield the ground mixture; and sterilizing the ground mixture.

2. The method of claim 1, wherein nebulizing the substance of interest is made by pressurization or ultrasound.

3. The method of claim 1, wherein the sterilizing is done through ultraviolet radiation at 260 nm, for 30 minutes.

4. The method of claim 1, wherein the egg product is selected from a group consisting of: albumin, yolk, shell, egg-derived fractions and combinations thereof.

5. The method of claim 1, wherein the egg product is albumin.

6. The method of claim 1, wherein the substance of interest is selected from a group consisting of: chemical substances, food products, cosmetics and combinations thereof.

7. The method of claim 6, wherein the chemical substance is a pharmaceutical.

8. The method of claim 7, wherein the pharmaceutical is selected from a group consisting of: urinary acidifiers, analgesics, androgens; anesthetics; anorexigens; antacids; anti-acne; Antadrenals; antianginal; antiarrhythmic; anti-arthritis; Anti-arthrosic; antiasthmatic; antibacterials; anti-coagulants; Anti-cholelithiasic; contraceptives; anticonvulsants; antidiarrheal; Anti-dyskinetic; antidiuretic; antidotes; antiemetics; antispasmodics; anti-spastics; antifibrotic; anti-flatulent; antifungals; anti-glaucomic; anti-gouty; anti-influenza; anthelmintics; Antihaemorrhagics; antihemorrhoidal; Antihyperkalemic; antihypercholesterolemic; antihyper-lipemic; Anti-hyperoxaluric; Anti-hyperpotassemic; Anti-hyperprolactemic; antihypertensives; Antihyperthyroidic; Antihhyperuricemic; Antihypocalcemic; Anthypocholester-loemic; antihypotensive; antihistamines; Anti-inflammatory; antiheadache; antileprosy; antilithic; antimalarials; antimy-asthenics; antifungals; antineoplastic; antirheumatic; Anti-scabies; antiseborrhoeic; antiseptics; antithyroid; antituber-culosis; antitussives; antiulcer; Antiurolithiasic; antivaricose; antivertiginosos; antivirals; Neuromuscular blockers; bronchodilators; capilaryprotectant; cardiotonic; cycloplegic; cytotoxic; cholelitholytics; decongestants; diuretics; emetics; escabicides; steroid; Gastric Motility stimulants; C.N.S. Stimulants; germicides; hypocholestero-laemiant; hypoglycemic; lipid-lowering; hormones; Dop-aminergic inhibitors; Gonadotrophe inhibitors; Childbirth inhibitors; Inhibitors of gastric secretions; immunosuppressants; laxatives; mydriatic; Miotic Myelosuppressives-; mucolytics; orexigens; oxytocics; pediculicide; placebos; prophylactics; and combinations thereof.

9. The method of claim 8, wherein the analgesic is acetylsalicylic acid.

10. The method of claim 8, wherein the anti-inflammatory is selected from a group consisting of: diclofenac, sodium naproxen, ketorolac and combinations thereof.

11. The method of claim 6, wherein the food product is selected from the group consisting of: proteins, carbohydrates, lipids, food supplements, vitamins, minerals, antioxidants, hormones, sweeteners, dye products and combinations thereof.

12. The method of claim 11, wherein the sweetener is *Estevia rebaudiana* Bertoni.

13. The method of claim 11, wherein the vitamin is riboflavin.

14. The method of claim 6, wherein the cosmetic is a protector from radiation.

15. The method of claim 1, wherein the substance of interest comprises solid particles, the method further comprising:

filtering the substance of interest; and dissolving the filtered substance of interest in an aqueous or hydroalcoholic solution.

16. The method of claim 1, further comprising:

compressing the ground mixture to form one or more tablets.

17. The method of claim 1, wherein the egg product is derived from a fowl's egg.

18. The method of claim 17, wherein the fowl is selected from a group consisting of a chicken, quail, turkey, duck, pheasant, goose, guinea-fowl, and ostrich.

19. The method of claim 17, wherein the fowl is a chicken.

20. The method of claim 1, wherein the egg product is dehydrated.

21. The method of claim 20, further comprising:

hydrating the egg product, with a hydrating liquid, in a ratio of 1:6, for around 5 minutes, with stirring at 50 rpm.

22. The method of claim 21, wherein the hydrating liquid is selected from a group consisting of: water, lipidic mixture, aqueous and hydro-alcoholic extract.

\* \* \* \* \*